United States Patent [19]
Lin et al.

[11] Patent Number: 5,766,913
[45] Date of Patent: Jun. 16, 1998

[54] CLONING, EXPRESSION AND NUCLEOTIDE SEQUENCE OF AN ALKALINE LIPASE GENE FROM PSEUDOMONAS PSEUDOALCALIGENES F-111

[75] Inventors: Shuen-Fuh Lin, Taipei; Chien-Ming Chiou, Gaushyong; Kuang-Hsiang Chuang, Taipei Hsien, all of Taiwan

[73] Assignee: Tatung Co., Ltd., Taipei, Taiwan

[21] Appl. No.: 606,888

[22] Filed: Feb. 26, 1996

[51] Int. Cl.⁶ .............................. C12N 9/20; C12N 1/20; C12N 15/00; C07H 21/04
[52] U.S. Cl. .............. 435/198; 536/23.2; 536/23.7; 435/69.1; 435/252.34; 435/320.1; 435/172.3; 530/350
[58] Field of Search ..................... 435/198, 69.1, 435/172.3, 320.1, 252.3, 252.31, 252.34; 536/23.2, 23.7

[56] References Cited

U.S. PATENT DOCUMENTS 5,278,066  1/1994  Andreoli et al. ............... 435/252.34

FOREIGN PATENT DOCUMENTS 0 218 272  4/1987  European Pat. Off. .

*Primary Examiner*—Robert A. Wax
*Assistant Examiner*—Tekchand Saidha
*Attorney, Agent, or Firm*—Fish & Richardson P.C.

[57] ABSTRACT

A DNA fragment obtained from *Pseudomonas pseudoalcaligenes* F-111, the DNA fragment comprises a base sequence of encoding alkaline lipase gene and a base sequence of controlling the expression of encoding alkaline lipase gene. This invention also discloses the process of using these DNA fragments.

4 Claims, 10 Drawing Sheets

```
           10         20         30         40         50         60
    GGATCCCCAG CAGGTCAGGA CTCCGACAAT CAGCGCGCCC AGGCCAAAGA AAGCCGCAAT
           70         80         90        100        110        120
    CAGCCCCGGG ACGAAGAATT CGGAAATCAG CAGGGCGAAC CCCAGTAGCA GCCAGAAGGC
          130        140        150        160        170        180
    ATACCCGTTG ACATAACTGC TCAGCAGCAT GATGACATCC TTGCATTAAC GGTGGCAGGC
          190        200        210        220        230        240
    AAAGCTGAGA GTCTACCAGA TTGCCCTGGC TCGGGGCGC TCAATCGGGT TTGCGGAACC
          250        260        270        280        290        300
    CATTCACAAT TTCGCTGCTG CTGACACACC CAAACTCTGA ATTACCGTTC ATCGGATTCA
          310        320        330        340        350        360
    TCCTGACAAT ATCCGGATGC CAGAGCGCAC GACTAATTGG TCACTTTTCA GCCGCCTAGG
          370        380        390        400        410        420
    TCAACCCCGC TGAACCCTGC GCCGCGCCTT CAATTCATCA CCAGGCCTGA CTATGCTCCC
          430        440        450        460        470        480
    GGACAGCCTC TGTGATGCAG TCAGAGACAC AACAACAATA AAACCGCACA AGGACTCGCA
          490        500        510        520        530        540
    TTATGCGCAA CAAGACTCGC GTCTCGCTCC GCCTCGGGCT GGCCACTACG CTGGGCATCA
          550        560        570        580        590        600
    GCACCCAGCC CAGGCCTTCC TGTTCGGCTC CTCGAACTAC ACCAAGACCC AGTACCCGAT
          610        620        630        640        650        660
    CGTCCTGACC CGCGGCATGC TCGGCTTCGA CAGCCTGCTT GGGGTCGACT ACTGGTACGG
          670        680        690        700        710        720
    CATTCCCTCA GCCCAGCGTA AAGACGGCGC CACCGTCTAC TTCACCGAAG TCAGCCAGCT
          730        740        750        760        770        780
    CGACACCTCC GAAGCCCGGG GTGAGCAACT GCTGACCCAG GTCGAGGAAA TCGTCGCCAT
          790        800        810        820        830        840
    CAGCGGCAAA CCCAAGGTCA ATCTGTTCGG CCACAGCCAT GGCGGGCCTA CCATCCGCTA
          850        860        870        880        890        900
    CGTTGCCGCC GTGGCCCCGG ATCTGGTCGC CTCGGTCACC AGCATTGGCG CGCCGCACAA
          910        920        930        940        950        960
    GGGTTCGGCC GCCGCCGACT TCATCCGCCA GGTGCCGGAA GGATCGGCCA GCGAAGCGAT
          970        980        990       1000       1010       1020
    TCTGGCCGGG ATCGTCAATG GTCTGGGTGC GCTGATCAAC TTCCTCTCCG GCAGCAGTTC
         1030       1040       1050       1060       1070       1080
    GGACACCCCA CAGAACTCGT TGGGCACGCT GGAGTCGCTG AACTCCGAAG GCGCCGCACG
         1090       1100       1110       1120       1130       1140
    GTTCAACGCC CGCTTCCCCC AAGGTGTGCC GACCAGCGCC TGCGGCGAGG GTGATTACGT
         1150       1160       1170       1180       1190       1200
    AGTCAATGGC GTGCGCTATT ACTCCTGGAG CGGCACCAGC CCGCTGACCA ACATACTCGA
         1210       1220       1230       1240       1250       1260
    CCCTTCCGAC CTGCTGCTCG GCGCCACCTC CCTGCCATTC GGTTTCGAGG CCAACGATGG
         1270       1280       1290       1300       1310       1320
```

FIG. 1A

```
TCTGGTCGGA CGCTGCAGCT CCCGGCTGGG TATGGTGATC CGCGACAACT ACCGGATGAA
    1330       1340       1350       1360       1370       1380
CCACCTGGAT GAGGTGAATC AGACCTTCGG GCTGACCAGC ATATTCGAGA CCAGCCCGGT
    1390       1400       1410       1420       1430       1440
ATCGGTCTAT CGCCAGCAAG CCAATCGCCT GAAGAACGCC GGGCTCTGAA ATAGGCTCCA
    1450       1460       1470       1480       1490       1500
CAACCAGACA GGGCTGGCCT CAGGGGCCAT GCACAGGTAC CGATATCGAC ATGAAGCCGC
    1510       1520       1530       1540       1550       1560
TGATTTATCT GCCGTTGCTA CTCGGCCTCG GCTGCTCGGC TGGCACCTGA GCACACCGAC
    1570       1580       1590       1600       1610       1620
ACCCAGCCCC TCCGCGCCCA CATCAACGCC GCTACAAGCC GGCAGTGAAC AACCCGCCAC
    1630       1640       1650       1660       1670       1680
AACTCCTGTG AGTCTGACCC GTCCGACCAC GCGCAGCACC GACCAGCACC TGCCCGCCTC
    1690       1700       1710       1720       1730       1740
ACTGCGCGAT ACCGACATCG ATGGTCAACT CGAAGTCGAC GCCCAGGGCA ATCTGGTGAT
    1750       1760       1770       1780       1790       1800
TACCGACCAA CTGCGTCACC TGTTCGATTA TTTCTTCAGC ACCGTCGGCG AACAGTCGTT
    1810       1820       1830       1840       1850       1860
CGAGCACCCC AGCAGCGCTA TCCGTGACTA TCTGGCCAGC CAGCTGCGTG ACGCGGCTCT
    1870       1880       1890       1900       1910       1920
GGCTCAGGCC CTGGATCTTC TGGATCGCTA TATCGACTAC AAAACTGAGC TGGTGGAGCT
    1930       1940       1950       1960       1970       1980
GGAGCGACGC TTCCCGATGG TGACCGAACT GGACGGCCTG CGCGCCCGCG AAGATGCCGT
    1990       2000       2010       2020       2030       2040
ACAACGCCTG CGCGCCAGTC TGTTCAACGC GCAGGAGCAC GCCGCCTTCT TCGCCAGCGA
    2050       2060       2070       2080       2090       2100
AGAGGTCTAT AACCAGTTCA CTCTTGAGCG TCTGGCGATA CTGCACGATC CGTCGCTGGA
    2110       2120       2130       2140       2150       2160
TCCGCAGACA CAGGCCGAAC GGATTGAACG GCTGCGCGAA GGGCTGCCCG ACGAGTTGCA
    2170       2180       2190       2200       2210       2220
ACAATTGCTG GTACCGCAAT TGCACCTGAC CCTGCGCCAC GACCCAGCAG TTGCTGACCA
    2230       2240       2250       2260       2270       2280
AGGTGCCGAG CCGGAACAGC TACGCCAGTT GCGCCTGAAC CTGTTCGGGC CTCAGGCAAC
    2290       2300       2310       2320       2330       2340
CGAGCGGCTG GAACGGCTGG ACCGCAACG CAGCGAATGG GATCAGCGCC TTGAGCGGTT
    2350       2360       2370       2380       2390       2400
CAATCGCGAA CGTCAGGCGA TCATCAGCCA GCCGGGCGCG TGGACAGCGA CAAGCAGGCC
    2410       2420       2430       2440       2450       2460
GCGATTGAGG CCTGCTGCAC GAGCAGTTCA GCGAGCACGA GCGCTCAGGG TCAATAGCCT
    2470       2480       2490       2500       2510       2520
GTTGGAACTC GATAGCCGCG CCGAACGCTA GGGAAACACT GATTAATTGC ACGTAAGCTC
    2530       2540       2550       2560       2570       2580
AATAGCCCGG TTGGCGCTGA CCTGTTCTGG ACCGTTAGAT GCCAGGGATG GCATCTAAGA
    2590       2600       2610       2620       2630       2640
```

FIG. 1B

```
GCGTACACGG ATGTATTTAC AGCGTGTCCA GAACAGGTCA GCGACAATTG GGCCAGCACC
    2650       2660       2670       2680       2690       2700
AAAACCGATT TAATCAGTGT TTCCCTAGCG AGCCTCTGAG AAACTACCTA ACACTTAATT
    2710       2720       2730       2740       2750       2760
GGCAATCTGG CGGTCCACCA GCCATCATCA GCTTGATGAT TGCGGAGGCC GTCATGCCAA
    2770       2780       2790       2800       2810       2820
TTCTGCGCTG CTGCTCCGCG CATTGCTGGG CCCGGTCTGG GCCGAGCGCA GCTATTCACC
    2830       2840       2850       2860       2870       2880
GGACGAAATA CTGACCTGGC AACAACGCAG TTTTGCCGGG CTGACCGACT ATCGACTCGT
    2890       2900       2910       2920       2930       2940
TGCCGACCAG TTGCCACCTC GGTCGCATGC
```

FIG. 1C

```
GGATTCATICTGACAATATGCGGATGCCAGAGCGCACGAC  TAATTGGTCAGTTTTCAGCCGCCTA
                                          Putative promoter GGTCAACCCCGCTGAACCCTGCGGCGCGCCTTCAATTCATCACC  AGGC  CTGACT.
                                              Putative S-D sequence
```

```
     -48                              -40
5'   ATG CTC CCG GAC AGC CTC TGT GAT GCA GTC AGA GAC ACA ACA ACA ATA AAA CCG
      M   L   P   D   S   L   C   D   A   V   R   D   T   T   T   I   K   P
     |
     Signal peptide (413 bp.)

-30                              -20
     CAC AAG GAC TCG CAT TAT GCG CAA CAA GAC TCG CGT CTC GCT CCG CCT CGG GCT
      H   K   D   S   H   Y   A   Q   Q   D   S   R   L   A   P   P   R   A

-10                                       -1   1
     GGC CAC TAC GCT GGG CAT CAG CAC CCA GCC CAG GCC TTC CTG TTC GGC TCC TCG
      G   H   Y   A   G   H   Q   H   P   A   Q   A   F   L   F   G   S   S
                                                         |
                                         563 bp. —┘    Mature alkaline lipase 10                                  20
     AAC TAC ACC AAG ACC CAG TAC CCG ATC GTC CTG ACC CGC GGC ATG CTC GGC TTC
      N   Y   T   K   T   Q   Y   P   I   V   L   T   R   G   M   L   G   F 30                                  40
     GAC AGC CTG CTT GGG GTC GAC TAC TGG TAC GGC ATT CCC TCA GCC CAG CGT AAA
      D   S   L   L   G   V   D   Y   W   Y   G   I   P   S   A   Q   R   K 50                                   60
     GAC GGC GCC ACC GTC TAC TTC ACC GAA GTC AGC CAG CTC GAC ACC TCC GAA GCC
      D   G   A   T   V   Y   F   T   E   V   S   Q   L   D   T   S   E   A 70
     CGG GGT GAG CAA CTG CTG ACC CAG GTC GAG GAA ATC GTC GCC ATC AGC GGC AAA
      R   G   E   Q   L   L   T   Q   V   E   E   I   V   A   I   S   G   K 80                                  90
     CCC AAG GTC AAT CTG TTC GGC CAC AGC CAT GGC GGG CCT ACC ATC CGC TAC GTT
      P   K   V   N   L   F   G   H   S   H   G   G   P   T   I   R   Y   V
                                   Active site 100                                 110
     GCC GCC GTG GCC CCG GAT CTG GTC GCC TCG GTC ACC AGC ATT GGC GCG CCG CAC
      A   A   V   A   P   D   L   V   A   S   V   T   S   I   G   A   P   H 120                                 130
     AAG GGT TCG GCC GCC GCC GAC TTC ATC CGC CAG GTG CCG GAA GGA TCG GCC AGC
      K   G   S   A   A   A   D   F   I   R   Q   V   P   E   G   S   A   S
```

FIG. 2A

```
                                        140                                                    150
GAA GCG ATT CTG GCC GGG ATC GTC AAT GGT CTG GGT GCG CTG ATC AAC TTC CTC
 E   A   I   L   A   G   I   V   N   G   L   G   A   L   I   N   F   L

160
TCC GGC AGC AGT TCG GAC ACC CCA CAG AAC TCG TTG GGC ACG CTG GAG TCG CTG
 S   G   S   S   S   D   T   P   Q   N   S   L   G   T   L   E   S   L 170                                            180
AAC TCC GAA GGC GCC GCA CGG TTC AAC GCC CGC TTC CCC CAA GGT GTG CCG ACC
 N   S   E   G   A   A   R   F   N   A   R   F   P   Q   G   V   P   T 190                                        200
AGC GCC TGC GGC GAG GGT GAT TAC GTA GTC AAT GGC GTG CGC TAT TAC TCC TGG
 S   A   C   G   E   G   D   Y   V   V   N   G   V   R   Y   Y   S   W 210                                        220
AGC GGC ACC AGC CCG CTG ACC AAC ATA CTC GAC CCT TCC GAC CTG CTG CTC GGC
 S   G   T   S   P   L   T   N   I   L   D   P   S   D   L   L   L   G 230                                        240
GCC ACC TCC CTG CCA TTC GGT TTC GAG GCC AAC GAT GGT CTG GTC GGA CGC TGC
 A   T   S   L   P   F   G   F   E   A   N   D   G   L   V   G   R   C

250
AGC TCC CGG CTG GGT ATG GTG ATC CGC GAC AAC TAC CGG ATG AAC CAC CTG GAT
 S   S   R   L   G   M   V   I   R   D   N   Y   R   M   N   H   L   D 260                                    270
GAG GTG AAT CAG ACC TTC GGG CTG ACC AGC ATA TTC GAG ACC AGC CCG GTA TCG
 E   V   N   Q   T   F   G   L   T   S   I   F   E   T   S   P   V   S 280                                    290
GTC TAT CGC CAG CAA GCC AAT CGC CTG AAG AAC GCC GGG CTC TGA  3'
 V   Y   R   Q   Q   A   N   R   L   K   N   A   G   L   *
                                                          └─ 1427 bp.
```

FIG. 2B

ATCGCCTGAAGAACGCCGGGCTC [TGA] AATAGGCTCCACAACCAGACAGGGCTGGCCTCAGGGGCC
Alkaline lipase (lip A) stop codon

```
     1                                          10
5' ATG CAC AGG TAC CGA TAT CGA CAT GAA GCC GCT GAT TTA TCT GCC GTT GCT ACT
    M   H   R   Y   R   Y   R   H   E   A   A   D   L   S   A   V   A   T
   1469 bp.
          20                                    30
   CGG CCT CGG CTG CTC GGC TGG CAC CTG AGC ACA CCG ACA CCC AGC CCC TCC GCG
    R   P   R   L   L   G   W   H   L   S   T   P   T   P   S   P   S   A 40                                        50
   CCC ACA TCA ACG CCG CTA CAA GCC GGC AGT GAA CAA CCC GCC ACA ACT CCT GTG
    P   T   S   T   P   L   Q   A   G   S   E   Q   P   A   T   T   P   V 60                                        70
   AGT CTG ACC CGT CCG ACC ACG CGC AGC ACC GAC CAG CAC CTG CCC GCC TCA CTG
    S   L   T   R   P   T   T   R   S   T   D   Q   H   L   P   A   S   L 80                                        90
   CGC GAT ACC GAC ATC GAT GGT CAA CTG GAA GTC GAC GCC CAG GGC AAT CTG GTG
    R   D   T   D   I   D   G   Q   L   E   V   D   A   Q   G   N   L   V

100
   ATT ACC GAC CAA CTG CGT CAC CTG TTC GAT TAT TTC TTC AGC ACC GTC GGC GAA
    I   T   D   Q   L   R   H   L   F   D   Y   F   F   S   T   V   G   E 110                                       120
   CAG TCG TTC GAG CAG GCC AGC AGC GCT ATC CGT GAC TAT CTG GCC AGC CAG CTG
    Q   S   F   E   Q   A   S   S   A   I   R   D   Y   L   A   S   Q   L 130                                           140
   CGT GAC GCG GCT CTG GCT CAG GCC CTG GAT CTT CTG GAT CGC TAT ATC GAC TAC
    R   D   A   A   L   A   Q   A   L   D   L   L   D   R   Y   I   D   Y 150                                         160
   AAA ACT GAG CTG GTG GAG CTG GAG CGA CGC TTC CCG ATG GTG ACC GAA CTG GAC
    K   T   E   L   V   E   L   E   R   R   F   P   M   V   T   E   L   D 170                                         180
   GGC CTG CGC GCC CGC GAA GAT GCC GTA CAA CGC CTG CGC GCC AGT CTG TTC AAC
    G   L   R   A   R   E   D   A   V   Q   R   L   R   A   S   L   F   N

190
   GCG CAG GAG CAC GCC GCC TTC TTC GCC AGC GAA GAG GTC TAT AAC CAG TTC ACT
    A   Q   E   H   A   A   F   F   A   S   E   E   V   Y   N   Q   F   T 200                                       210
   CTT GAG CGT CTG GCG ATA CTG CAC GAT CCG TCG CTG GAT CCG CAG ACA CAG GCC
    L   E   R   L   A   I   L   H   D   P   S   L   D   P   Q   T   Q   A 220                                         230
   GAA CGG ATT GAA CGG CTG CGC GAA GGG CTG CCC GAC GAG TTG CAA CAA TTG CTG
    E   R   I   E   R   L   R   E   G   L   P   D   E   L   Q   Q   L   L
```

FIG. 3A

```
                                      240                                              250
    GTA CCG CAA TTG CAC CTG ACC CTG CGC CAC GAC CCA GCA GTT GCT GAC CAA GGT
     V   P   Q   L   H   L   T   L   R   H   D   P   A   V   A   D   Q   G 260                                              270
    GCC GAG CCG GAA CAG CTA CGC CAG TTG CGC CTG AAC CTG TTC GGG CCT CAG GCA
     A   E   P   E   Q   L   R   Q   L   R   L   N   L   F   G   P   Q   A

280
    ACC GAG CGG CTG GAA CGG CTG GAC CGC CAA CGC AGC GAA TGG GAT CAG CGC CTT
     T   E   R   L   E   R   L   D   R   Q   R   S   E   W   D   Q   R   L 290                                              300
    GAG CGG TTC AAT CGC GAA CGT CAG GCG ATC ATC AGC CAG CCG GGC GCG TGG ACA
     E   R   F   N   R   E   R   Q   A   I   I   S   Q   P   G   A   W   T 310                                                      320
    GCG ACA AGC AGG CCG CGA TTG AGG CCT GCT GCA CGA GCA GTT CAG CGA GCA CGA
     A   T   S   R   P   R   L   R   P   A   A   R   A   V   Q   R   A   R 330                                              340
    GCG CTC AGG GTC AAT AGC CTG TTG GAA CTC GAT AGC CGC GCC GAA CGC TAG  3'
     A   L   R   V   N   S   L   L   E   L   D   S   R   A   E   R   *
```

CLONING, EXPRESSION AND NUCLEOTIDE SEQUENCE OF AN ALKALINE LIPASE GENE FROM PSEUDOMONAS PSEUDOALCALIGENES F-111

FIELD OF THE INVENTION

This invention is related to the DNA fragment of the novel microorganism used in producing the alkaline lipase.

BACKGROUND OF THE INVENTION

Lipase is a very important metabolic enzyme for ordinary biological body, it can hydrolyze fat to produce free fatty acid. Recently, it has been found that lipase not only can decompose fat but also can carry out many different reactions. Lipase is more stable in organic solvent, and can even undergo versatile reactions under 100° C. Many breakthroughs in the research and development in this area has attracted wide attention from industries, such as pharmaceutical, lipid, perfume, chemical, pesticide, food, etc.

The alkaline lipase can even be added into detergent as another application. Many years ago products with the addition of alkaline thrombase brought up the so called "detergent revolution". To increase cleaning ability by using alkaline lipase to clean grease spot on the clothes is another industrial application of the alkaline lipase. See satsuki, T., et al., Bio. Industry, 7:501 (1990).

SUMMARY OF THE INVENTION

The bacteria strain used in the present invention is the *Pseudomonas pseudoalcaligenes* F-111 (deposit No. CCRC 910008, Food Industry Research and Development Institute, Taiwan, R.O.C.).

The present invention is related to a DNA fragment obtained from the chromosome of the *Pseudomonas pseudoalcaligenes* F-111. Said DNA fragment comprises a base sequence of the encoding alkaline lipase gene and a base sequence of controlling the expression of the encoding alkaline lipase gene.

The present invention is also related to the process of using the above-mentioned DNA fragment to produce alkaline lipase, which comprises the steps of:

(a) isolating chromosome DNA from the *Pseudomonas pseudoalcaligenes* F-111;

(b) using the restriction enzyme Sau 3A to partially digest the chromosome DNA of *Pseudomonas pseudoalcaligenes* F-111 in order to obtain the DNA fragment comprising the base sequence of the encoding alkaline lipase gene and the base sequence of controlling the expression of the encoding alkaline lipase gene;

(c) implanting the DNA fragment into a plasmid (such as pGEM-3Zf(+1)) which can be expressed in the *E. coli* in order to obtain a carrier;

(d) transforming the carrier into the *E. coli*;

(e) cultivating the transformed *E. coli*; and (f) isolating the alkaline lipase.

Other features and advantages of the present invention will be apparent from the following drawings and description of the preferred embodiments.

BRIEF DESCRIPTION OF THE DRAWINGS

FIG. 1 is a diagram showing the base sequence of the DNA fragment obtained from the chromosome of the *Pseudomonas pseudoalcaligenes* F-111;

FIG. 2 is a diagram showing the base sequence of the encoding alkaline lipase gene (denominated as Lip A);

FIG. 3 is a diagram showing the base sequence of controlling the expression of the encoding alkaline lipase gene (denominated as Lip B);

DESCRIPTION OF THE PREFERRED EMBODIMENTS

The present invention provides a DNA fragment obtained from the chromosome of the *Pseudomonas pseudoalcaligenes* F-111. Said DNA fragment comprises a base sequence of the encoding alkaline lipase gene and a base sequence of controlling the expression of the encoding alkaline lipase gene. Said DNA fragment comprises the base sequence as showing in FIG. 1, in which the base sequence of the encoding alkaline lipase gene (denominated as Lip A) is showing in FIG. 2, and the base sequence of controlling the expression of the encoding alkaline lipase gene (denominated as Lip B) is showing in FIG. 3.

(1) Gene Cloning Strategy

Figure 5:
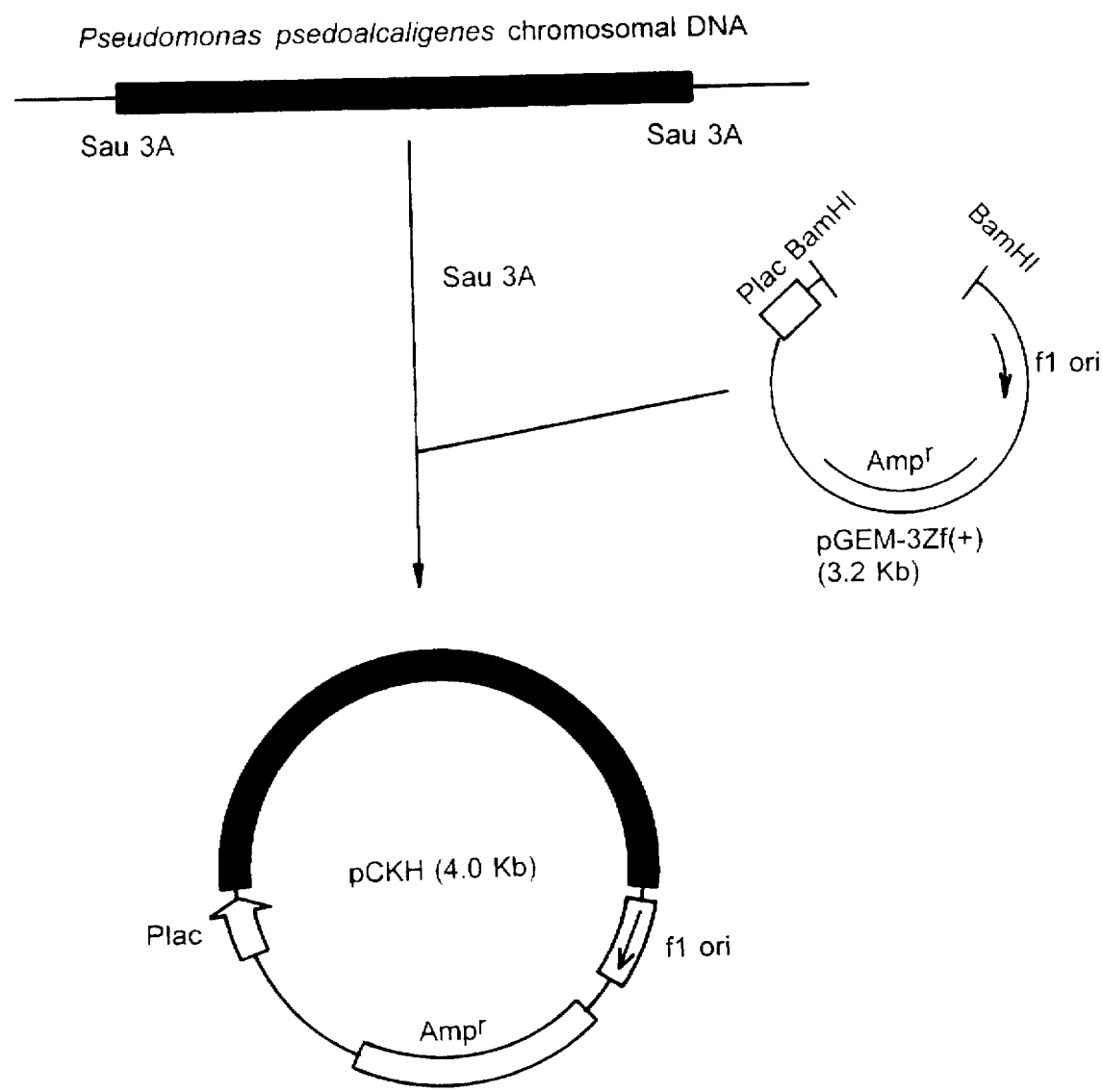
FIG. 5 is a diagram showing the flowchart of preparation of plasmid pCHK4.

The gene cloning strategy of this experiment is shown in FIG. 5, which comprises chopping the chromosome DNA of *Pseudomonas pseudoalcaligenes* F-111 with Sau 3A portion; using pGEM-3Zf(+) plasmid to undergo shutgun cloning in the *E. coli* host; and isolating transformed strains capable of expressing gene of code-containing alkaline lipase from the agar gel culture medium in tributyrin.

(2) Cloning of Gene

The plasmids suitable for DNA insertion includes pGEM-3Zf(+) [Promega, U.S.A.], pBR322 [Gene, 2:95(1977)], pBR325 [Gene, 4:121(1978)] and pUC13 [Gene, 19:259, (1982)] obtained from *E. coli*; any other plasmid which can replicate and maintain in the host may also be used. The method of inserting this DNA into the plasmid includes, for example, the method disclosed in Miniatis, T. et al., Molecular Cloning, Cold Spring Harbor Laboratory, p.239 (1982). Examples of using *E. coli* include, for example, *E. coli* DH10B [Lorow, D., and Jessee, J., (1990) Focus, 12:19], HB101 [J. Mol. Biol., 41, 459 (1969)], K12, DH1 [Proc. Natl. Acad. Sci., U.S.A., 60, 160 (1968)].

The methods of using plasmid to transform host include, for example, the Calcium Chloride Method disclosed in Miniatis, T. et al., Molecular Cloning, Cold Spring Harbor Laboratory, p. 239 (1982), or the Calcium Chloride/Rubidium Chloride Method. Said methods can be used to obtain *Pseudomonas pseudoalcaligenes* F-111 gene library which comprises the encoding alkaline lipase DNA.

Whenever necessary or appropriate, this cloned encoding alkaline lipase DNA can be sub-cloned to plasmids such as pBR322, pUC12, pUC13, pUC18, and pUC19.

(3) Screening of Encoding Alkaline Lipase Gene

The expression of alkaline lipase gene is shown directly by using enzymatic activity which comprises isolating bacteria strain capable of generating pellucid ring from the agar gel culture medium in tributyrin (1% tributyrin, 1% Bacto tryptone, 0.5% yeast extract, 0.5% sodium chloride and 0.005% ampicillin, emulsified homogeneously by a blender), or according to the *Pseudomonas pseudoalcali-* genes F-111 using a chemically synthesized oligonucleotide as the probe to undergo the colony hybridization process.

(4) Influence of pCKH4 Plasmid and its Subclone on the Expression of Alkaline Lipase Gene In order to understand the position of alkaline lipase gene in the pCKH4 plasmid for eliminating test and cotransformation effects, as shown in Table I, the inventors have found that the expression of alkaline lipase gene requires the assistance of another controlling DNA fragment. This transacting phenomena exist in many Pseudomonas-type lipase [Jane Gilbert, E., (1993) Enzyme Micrib. Technol., 15:634]. The base sequence of controlling expression of the encoding alkaline lipase gene is approximately located between 1.5 to 2.9 Kbp. Table 1 shows the variation between pCKH4 plasmid and its subclone to the alkaline lipase expression.

TABLE 1

| Name of plasmid | Location | Size (alkaline pair) | Activity (expression of pellucid ring) |
|---|---|---|---|
| PCKH4 | full length | 4000 | + |
| PCKH-EE 3.9 | 0.1–4.0 | 3900 | + |
| PCKH-PE 2.7 | 1.3–4.0 | 2700 | − |
| PCKH-EP 1.3 | 0.0–1.3 | 1300 | − |
| PCKH-SS 2.2 | 0.7–2.9 | 2200 | − |
| PCKH-XC 1.7 | 0.0–1.7 | 1700 | − |
| PCKH-CSa2.3 | 1.7–4.0 | 2300 | − |
| PCKH-BB2.0 | 0.0–2.0 | 2000 | − |
| PCKH-BE2.0 | 2.0–4.0 | 2000 | − |
| PCKH-ES0.7 | 0.0–0.7 | 700 | − |
| PCKH-HER2.5 | 1.5–4.0 | 2500 | − |
| PCKH-PE2.7 + PCKH-XC1.7 | — | — | + |
| PCKH-XC1.7 +! PCKH-CSa2.3 | — | — | − |
| PCKH-XC1.7 + PCKH-HER2.5 | — | — | + |
| PCKH-SS2.2 + PCKH-XC1.7 | — | — | + |

B: BamHI, C: ClaI, E: EcoRI, ER: EcoRV, H: HindIV, P: PstI, S: SphI, Sa: SacI, X: XbaI.

(5) Identification of the Base Sequence of Encoding Alkaline Lipase Gene

Figure 4:
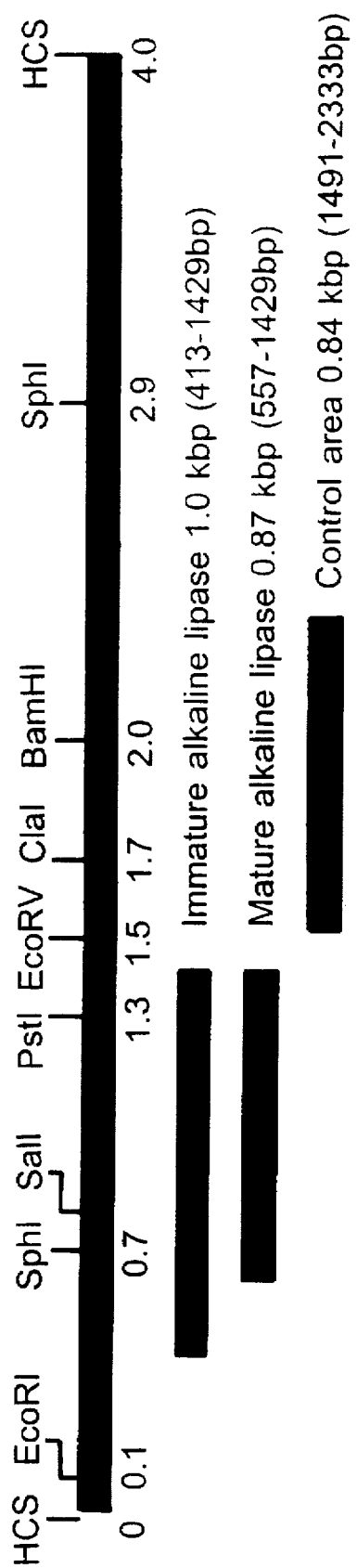
FIG. 4 is a diagram showing the cross-section of restriction enzyme containing the gene segment of the encoding alkaline lipase.

The dideoxy sequencing method [Sanger, F., Nicklen, S., and Coulson, A. R., 1979, Proc. Natl. Acad. Sci., 74:5463] was used to discharge 2910 basic pairs of sequence of the obtained DNA. The base sequence was then compared with known amino acid sequence of alkaline lipase. The test results have shown that the existing encoding alkaline lipase gene is a complete Open Reading Frame (ORF) sequence Lip A (413 to 1426 bps) which can transcribe 338 proteins composed of amino acids. By comparing with N-terminal sequence of protein and deducting secretion signal sequence, the inventors reach the conclusion that the complete sequence of a mature alkaline lipase comprises 290 amino acid sequences which starts from F-L-F-G-S-S (SEQ ID NO. 6). The calculated molecular weight is 30,826 Dalton which is close to the enzyme molecular weight of 32,000 Dalton measured by SDS-PAGE. The DNA of encoding alkaline lipase obtained in the following Example 1 of the invention is a typical example of DNA fragment of encoding alkaline lipase in which the cross section of its restriction enzyme is shown in FIG. 4.

(6) Identification of the Base Sequence of Controlling the Expression of Encoding Alkaline Lipase Gene According to the test results of transformed strain to the enzyme activity in Example 3, the gene expression of encoding alkaline lipase requires the assistance of another DNA fragment. According to Example 3 (Table 1), the gene sequence of encoding alkaline lipase is located between 1.5 to 2.9 Kbp; another base sequence Lip B (1469–2491 bp) controlling the gene expression of alkaline lipase can transcribe 340 residues of amino acid.

EXAMPLE 1

Purification of the Chromosome DNA of *Pseudomonas pseudoalcaligenes* F-111

To a one liter Erlenmeyer flask which contains 400 ml LB nutrient broth was added *Pseudomonas pseudoalcaligenes*. The mixture was oscillated at 37° C. for 24 hours, then centrifuged with 6,000 rpm at 4° C. to obtain cell precipitate. The obtained cell precipitate was dispersed by adding 36 ml of TE buffer solution (pH 8), followed by adding proteidin to obtain a final concentration of 1 mg/ml; slowly oscillating at 37° C. for 30 minutes, then added with SDS to obtain a concentration of 1%; gently rotating the mixture at 60° C. for 30 minutes, then added with equal volume of phenol and chloroform (volume ratio 1:1); slowly rotating the mixture for 60 minutes, then the solution was centrifuged with 9,000 rpm for 20 minutes to extract out the DNA dissolved in water layer. The operation is repeated for three times; add 1/10 volume of 3M potassium acetate and two times in volume of icy ethanol to the DNA solution to precipitate the DNA; use centrifugation to collect the precipitated DNA. The DNA precipitate was washed by 70% ethanol, vacuum dried, added with 2 ml of distilled water to dissolve the DNA, followed by stored at −20° C.

EXAMPLE 2

Cloning of the Encoding Alkaline Lipase Gene (A) Preparation of Gene Library (a) Using restriction enzyme Sau3AI to partially digest the chromosome DNA of *Pseudomonas pseudoaligenes* F-111 which is purified from Example 1. A reaction mixture system comprising 33 mM Tris-acetate buffer solution (pH 7.9), 10 mM magnesium acetate, 66 mM potassium acetate, 0.5 mM dithiothreitol, 10 µg chromosome DNA and 1.2 units of active Sau 3A, with total volume of 200 µl, was allowed to undergo reactions at 37° C. for 20 minutes, followed by treated with phenol-chloroform. The reaction mixture was removed of protein, added with two times in volume of ethanol to recover the digested DNA.

(b) The pGEM-3Zf(+) carrier DNA(Promega U.S.A.) was allowed to react in a reaction system, which comprises 10 mM Tris-HCl buffer solution (pH 8.0), 5 mM magnesium chloride, 100 mM sodium chloride, 1 mM dithiothreitol, 1 µg chromosome DNA and 1 unit of active BamHI, with total volume of 20 µl, at 37° C. for 2 hours. The reaction mixture was treated with phenol-chloroform, removed with protein, and then added with two times in volume of ethanol to recover the digested DNA.

(c) The chromosome DNA 500 ng obtained from the step (a) and the pGEM-3Zf(+) carrier DNA 100 ng obtained from the step (b) were allowed to undergo overnight joining reaction at 4° C. in a reaction system, which comprises 66 mM Tris-CHl buffer solution (pH 7.5), 5 mM magnesium chloride, 1 mM dithiothreitol, 1 mM ATP and 1 unit of active T4 DNA ligase, with a total volume of 20 µl, followed by treating with the calcium chloride method proposed by Mandal, et. al. [Mandal, M., and Higa, A., 1970, J. Miol., 53:159] to be fed into DH 10 B *colibacillus*, followed by coating it on the LB agar gel culture medium comprising X-gal and ampicillin, then selecting monostrains with white bacterial plaque. At the end of the experiment, approximately 2000 strains of transformed bacterial strain were obtained.

(B) Screening of Code-containing Alkaline Lipase Gene

Figure 6:
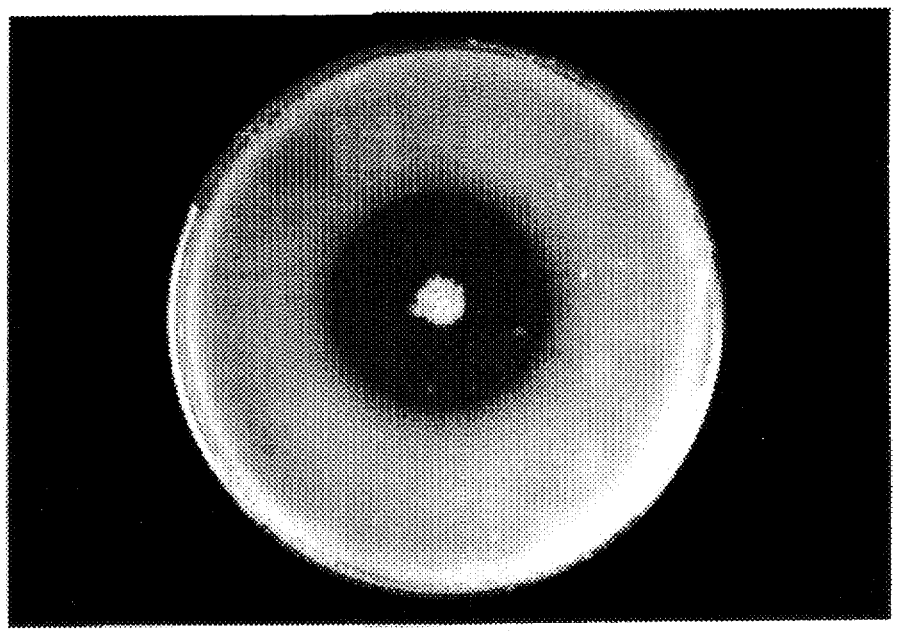
FIG. 6 is a diagram showing the TIT-7 cloning strain sieving agar gel culture medium in tributyrin.

By using toothpicks the 2,000 or so transformed strains are dotted onto the agar gel culture medium in tributyrin (1% tributyrin, 1% Bacto tryptone, 0.5% yeast extract, 0.5% sodium chloride and 0.005% ampicillin, emulsified homogeneously by a blender), and the bacteria strains capable of generating pellucid ring are selected. Approximately 10 strains of active transformed bacteria strain were obtained. After purification and cloning, one transformed bacteria strain (nomenclature as TIT-7) shows significant pellucid ring on the agar gel culture medium in tributyrin (see FIG. 6) which may contain the encoding alkaline lipase gene.

The method proposed by Birnboim, et al. [Birnboim, H. C., and Doly, J., 1979, Nuclei AcidRes., 7:715.] was used to withdraw the plasmid DNA of TIT-7 transformed strain. The result shows that the size of DNA withdrawn from the plasmid determined on the agar gel is 7.2 Kbp. After deducting the size of pGEM-3Zf(+) carrier DNA (3.2 Kbp), the size of chromosome DNA inserted in the pGEM-3Zf(+) carrier is 4.0 kbp. According to its size, the plasmid withdrawn from the TIT-7 transformed bacteria strain is nomenclature as pCKH4.

EXAMPLE 3

Controlling Behavior of the Transformed Bacteria Strain

In order to identify the nucleotide sequence, the atlas of pCKH4 plasmid was used to perform subcloning of each fragment. After treatments of different restriction enzymes, 10 different subcloned strains were obtained. Comparing their enzyme activity by observing their growth in tributyrin culture medium, the results shown in Table 1 indicate that, besides the pCKH-EE3.9 plasmid capable of showing activity, the rest of plasmids were unable to show enzyme activity. It is presumed that this gene expression requires the help of other proteins. When other subcloned plasmids are mixed and fed into the HB 10D host to undergo cotransformation, the cotransformation result of plasmids pCKH-PE2.7 and pCKH-XC1.7 shows that the control gene might locate after 1.3 Kbp; the cotrsnsformation result of plasmids pCKH-XC1.7 and pCKH-CSa2.3 shows that the control gene might locate before 1.7 Kbp; the cotransformation result of plasmids pCKH-XC1.7 and pCKH-HER2.5 shows that the control gene might locate after 1.5 Kbp; and the cotransformation result of plasmids of pCKH-SS2.2 and pCKH-XC1.7 shows that the control gene might locate before 2.9 Kbp.

EXAMPLE 4

Identification of the Base Sequence of Encoding Alkaline Lipase Gene

The DNA of pCKH4 subcloned bacteria strains were withdrawn and measured by the dideoxy sequencing method [Sanger, F., Nicklen, S., and Coulson, A. R., 1979, Proc. Natl. Acad. Sci., 74:5463] to determine the sequence of DNA insertion part. During the full length of 4000 nucleotides, 2910 nucleotides have been identified for their sequence in which two ORF are separately at 413 to 1429 bp (Lip A) and 1491 to 2491 bp (Lip B). The two ORFs are spaced out for only 41 pairs of base groups and there is a cutting position (GATATC) of EcoRV restriction enzyme located on the partial amino acid sequence of base 5' terminal sequence which matches the first 20 amino acid sequences of N-terminal of the purified alkaline lipase: Phe-Leu-Phe-Gly-Ser-Ser-Asn-Tyr-Thr-Lys-Thr-Gln-Tyr-Pro-Ile-Val-Leu-Thr-Arg-Gly (SEQ ID NO.7). The complete LipA gene comprises (1) a 5'-terminal control segment, such as initiator, TAATTGGTCACTTTTCAGCC (SEQ ID NO.8) [Deretic V., et al (1988) Bio/Technology 7:1249] and Shine-Dalgarno sequence, AGGC; (2) a secretion signal sequence, which is a peptide of 48 amino acids [V. Heijne, G. V., (1988) Nucleic Acids Res., 14:4683]; and (3) a structural gene which is a DNA sequence of encoding alkaline lipase comprising a common active center of lipase, G-H-S-H-G (SEQ ID NO. 9) [Winkler, F. K., et al, (1990) Nature, 343:771].

Based on these characteristics, the encoding alkaline lipase gene shall locate in the Lip A. The complete encoding alkaline lipase gene sequence (413 to 1426 bps), after deducting the secretion signal sequence, can transcribe proteins composed of 290 amino acids. The actual molecular size is 30,826 which is close to the size of 32,000 measured by the SDS-PAGE.

EXAMPLE 5

Identification of the Base Sequence of Controlling the Expression of Encoding Alkaline Lipase Gene According to Example 3 (Table 1), the base sequence of encoding alkaline lipase gene is located between 1.5 to 2.9 Kbp. And in this area there is another LipB (1469–2491) which is only 61 base groups away from the encoding alkaline lipase gene (ORF 1). It is presumed that the control expression gene and the encoding alkaline lipase gene are associated with each other and share the same initiator and Shine-Dalgarno sequence. There is no similarity between this base sequence of control expression gene and the known Pseudomonas alkaline gene sequence [Jane Gilbert, E., (1993) Enzyme Microbial. Technol., 15:634]. Therefore, the base sequence of control expression gene is a new control sequence.

EXAMPLE 6

Using E. coli Transformed Bacteria Strain (TIT-7) to Produce Alkaline Lipase

Figure 7:
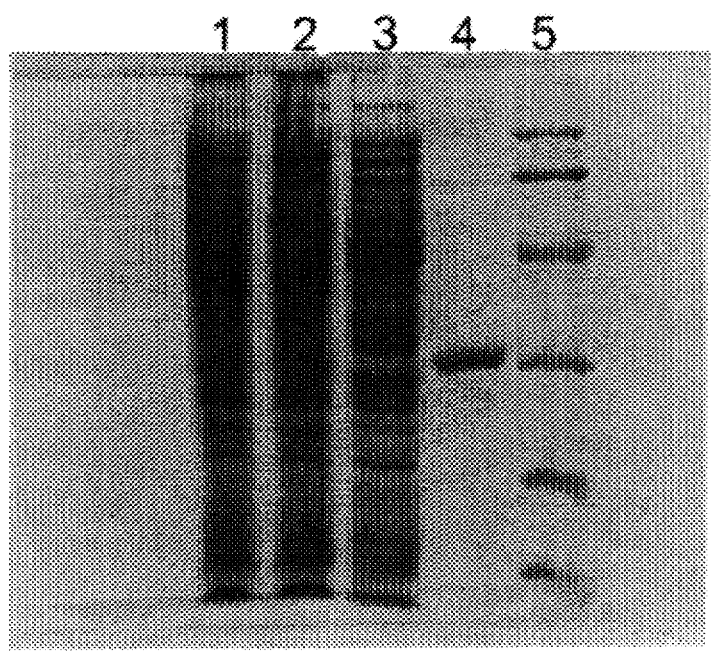
FIG. 7 is a diagram showing the SDS-polyacrylamide electrophoresis of TIT-7 cloning strain producing alkaline lipase.

The E. coli transformed bacteria strains (TIT-7) were selected by using bamboo toothpick, then implanted into 10 ml of LB culture medium containing ampicillin (50 µg/ml), followed by cultivating at 37° C. for 18 hours. 0.5 ml of culture was transferred to 50 ml of LB culture medium containing ampicillin (50 µg/ml) to be cultured at 37° C. for 5 hours; the solution was added with 0.5 ml of 0.1M IPTG (Isopropyl β-thiogalactose glucopyraoside) (final concentration 1 mM), followed by cultivating for 5 hours. Cells were collected (10,000 rpm, 20 minutes) and suspended in 20 ml Tris-HCl buffer solution (50 mM, pH 8.5) to receive ultrasonic treatment for 20 minutes; centrifugation (10,000 rpm, 20 minutes) was used to remove cell fractures. The upper layer clear liquid was tested by a known method to measure its alkaline lipase activity. The FIG. 7 shows the SDS-polyacrylamide electrophoresis results (1,2 are TIT cloning strain, 3 is the E. coli host, 4 is the purified alkaline lipase, 5 is the marker of molecular weight). The molecular weight of the material produced by the TIT cloning strain is about 32,000 Dalton and the additional protein color band can not be formed by the DH10B host.

---

What is claimed is:

1. An isolated DNA comprising:

a first nucleotide sequence encoding an alkaline lipase and being identical to SEQ ID NO:1; and a second nucleotide sequence controlling the expression of the alkaline lipase and being identical to the region between and including nucleotides 27 and 1088 of SEQ ID NO:4.

2. The DNA of claim 1, wherein the DNA is obtained from *Pseudomonas pseudoalcaligenes* F-111.

3. A process of producing an alkaline lipase, the process comprising:
   (a) isolating a chromosome DNA from *Pseudomonas pseudoalcaligenes* F-111;
   (b) using the restriction enzyme Sau 3A to partially digest said chromosome DNA in order to obtain a DNA fragment which comprises a first nucleotide sequence encoding an alkaline lipase and a second nucleotide sequence controlling the expression of said alkaline lipase;
   (c) inserting said DNA fragment into a plasmid which can be expressed in a *E. coli* host cell in order to obtain a carrier;
   (d) transforming said carrier into the *E. coli* host cell;
   (e) cultivating the transformed *E. coli* host cell; and
   (f) isolating the alkaline lipase from the cultivated *E. coli* host cell.

4. The process of claim 3, wherein said plasmid is PGEM-3Zf(1+1).

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2910 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GGATCCCCAG CAGGTCAGGA CTCCGACAAT CAGCGCGCCC AGGCCAAAGA AAGCCGCAAT      60
CAGCCCCGGG ACGAAGAATT CGGAAATCAG CAGGGCGAAC CCCAGTAGCA GCCAGAAGGC     120
ATACCCGTTG ACATAACTGC TCAGCAGCAT GATGACATCC TTGCATTAAC GGTGGCAGGC     180
AAAGCTGAGA GTCTACCAGA TTGCCCTGGC TCGGGGCGC  TCAATCGGGT TTGCGGAACC     240
CATTCACAAT TTCGCTGCTG CTGACACACC CAAACTCTGA ATTACCGTTC ATCGGATTCA     300
TCCTGACAAT ATCCGGATGC CAGAGCGCAC GACTAATTGG TCACTTTTCA GCCGCCTAGG     360
TCAACCCCGC TGAACCCTGC GCCGCGCCTT CAATTCATCA CCAGGCCTGA CTATGCTCCC     420
GGACAGCCTC TGTGATGCAG TCAGAGACAC AACAACAATA AAACCGCACA AGGACTCGCA     480
TTATGCGCAA CAAGACTCGC GTCTCGCTCC GCCTCGGGCT GGCCACTACG CTGGGCATCA     540
GCACCCAGCC CAGGCCTTCC TGTTCGGCTC CTCGAACTAC ACCAAGACCC AGTACCCGAT     600
CGTCCTGACC CGCGGCATGC TCGGCTTCGA CAGCCTGCTT GGGGTCGACT ACTGGTACGG     660
CATTCCCTCA GCCCAGCGTA AGACGGCGC  CACCGTCTAC TTCACCGAAG TCAGCCAGCT     720
CGACACCTCC GAAGCCCGGG GTGAGCAACT GCTGACCCAG GTCGAGGAAA TCGTCGCCAT     780
CAGCGGCAAA CCCAAGGTCA ATCTGTTCGG CCACAGCCAT GGCGGGCCTA CCATCCGCTA     840
CGTTGCCGCC GTGGCCCCGG ATCTGGTCGC CTCGGTCACC AGCATTGGCG CGCCGCACAA     900
GGGTTCGGCC GCCGCCGACT TCATCCGCCA GGTGCCGGAA GGATCGGCCA GCGAAGCGAT     960
TCTGGCCGGG ATCGTCAATG GTCTGGGTGC GCTGATCAAC TTCCTCTCCG GCAGCAGTTC    1020
GGACACCCCA CAGAACTCGT TGGGCACGCT GGAGTCGCTG AACTCCGAAG GCGCCGCACG    1080
GTTCAACGCC CGCTTCCCCC AAGGTGTGCC GACCAGCGCC TGCGGCGAGG GTGATTACGT    1140
AGTCAATGGC GTGCGCTATT ACTCCTGGAG CGGCACCAGC CCGCTGACCA ACATACTCGA    1200
CCCTTCCGAC CTGCTGCTCG GCGCCACCTC CCTGCCATTC GGTTTCGAGG CCAACGATGG    1260
TCTGGTCGGA CGCTGCAGCT CCCGGCTGGG TATGGTGATC CGCGACAACT ACCGGATGAA    1320
CCACCTGGAT GAGGTGAATC AGACCTTCGG GCTGACCAGC ATATTCGAGA CCAGCCCGGT    1380
ATCGGTCTAT CGCCAGCAAG CCAATCGCCT GAAGAACGCC GGGCTCTGAA ATAGGCTCCA    1440
CAACCAGACA GGGCTGGCCT CAGGGGCCAT GCACAGGTAC CGATATCGAC ATGAAGCCGC    1500
TGATTTATCT GCCGTTGCTA CTCGGCCTCG GCTGCTCGGC TGGCACCTGA GCACACCGAC    1560
ACCCAGCCCC TCCGCGCCCA CATCAACGCC GCTACAAGCC GGCAGTGAAC AACCCGCCAC    1620
AACTCCTGTG AGTCTGACCC GTCCGACCAC GCGCAGCACC GACCAGCACC TGCCCGCCTC    1680
ACTGCGCGAT ACCGACATCG ATGGTCAACT GGAAGTCGAC GCCCAGGGCA ATCTGGTGAT    1740
TACCGACCAA CTGCGTCACC TGTTCGATTA TTTCTTCAGC ACCGTCGGCG AACAGTCGTT    1800
```

| | | | | | |
|---|---|---|---|---|---|
| CGAGCAGGCC | AGCAGCGCTA | TCCGTGACTA | TCTGGCCAGC | CAGCTGCGTG | ACGCGGCTCT | 1860 |
| GGCTCAGGCC | CTGGATCTTC | TGGATCGCTA | TATCGACTAC | AAAACTGAGC | TGGTGGAGCT | 1920 |
| GGAGCGACGC | TTCCCGATGG | TGACCGAACT | GGACGGCCTG | CGCGCCCGCG | AAGATGCCGT | 1980 |
| ACAACGCCTG | CGCGCCAGTC | TGTTCAACGC | GCAGGAGCAC | GCCGCCTTCT | TCGCCAGCGA | 2040 |
| AGAGGTCTAT | AACCAGTTCA | CTCTTGAGCG | TCTGGCGATA | CTGCACGATC | CGTCGCTGGA | 2100 |
| TCCGCAGACA | CAGGCCGAAC | GGATTGAACG | GCTGCGCGAA | GGGCTGCCCG | ACGAGTTGCA | 2160 |
| ACAATTGCTG | GTACCGCAAT | TGCACCTGAC | CCTGCGCCAC | GACCCAGCAG | TTGCTGACCA | 2220 |
| AGGTGCCGAG | CCGGAACAGC | TACGCCAGTT | GCGCCTGAAC | CTGTTCGGGC | CTCAGGCAAC | 2280 |
| CGAGCGGCTG | GAACGGCTGG | ACCGCCAACG | CAGCGAATGG | GATCAGCGCC | TTGAGCGGTT | 2340 |
| CAATCGCGAA | CGTCAGGCGA | TCATCAGCCA | GCCGGGCGCG | TGGACAGCGA | CAAGCAGGCC | 2400 |
| GCGATTGAGG | CCTGCTGCAC | GAGCAGTTCA | GCGAGCACGA | GCGCTCAGGG | TCAATAGCCT | 2460 |
| GTTGGAACTC | GATAGCCGCG | CCGAACGCTA | GGGAAACACT | GATTAATTGC | ACGTAAGCTC | 2520 |
| AATAGCCCGG | TTGGCGCTGA | CCTGTTCTGG | ACCGTTAGAT | GCCAGGGATG | CATCTAAGA | 2580 |
| GCGTACACGG | ATGTATTTAC | AGCGTGTCCA | GAACAGGTCA | GCGACAATTG | GCCAGCACC | 2640 |
| AAAACCGATT | TAATCAGTGT | TTCCCTAGCG | AGCCTCTGAG | AAACTACCTA | ACACTTAATT | 2700 |
| GGCAATCTGG | CGGTCCACCA | GCCATCATCA | GCTTGATGAT | TGCGGAGGCC | GTCATGCCAA | 2760 |
| TTCTGCGCTG | CTGCTCCGCG | CATTGCTGGG | CCCGGTCTGG | GCCGAGCGCA | GCTATTCACC | 2820 |
| GGACGAAATA | CTGACCTGGC | AACAACGCAG | TTTTGCCGGG | CTGACCGACT | ATCGACTGGT | 2880 |
| TGCCGACCAG | TTGCCACCTC | GGTCGCATGC | | | | 2910 |

( 2 ) INFORMATION FOR SEQ ID NO:2:

( i ) SEQUENCE CHARACTERISTICS:
        ( A ) LENGTH: 1136 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 120..1136

( x i ) SEQUENCE DESCRIPTION: SEQ ID NO:2:

| | | | | | |
|---|---|---|---|---|---|
| GGATTCATCC | TGACAATATC | CGGATGCCAG | AGCGCACGAC | TAATTGGTCA | CTTTTCAGCC | 60 |
| GCCTAGGTCA | ACCCCGCTGA | ACCCTGCGCC | GCGCCTTCAA | TTCATCACCA | GGCCTGACT | 119 |

```
ATG CTC CCG GAC AGC CTC TGT GAT GCA GTC AGA GAC ACA ACA ACA ATA      167
Met Leu Pro Asp Ser Leu Cys Asp Ala Val Arg Asp Thr Thr Thr Ile
        -45                 -40                 -35

AAA CCG CAC AAG GAC TCG CAT TAT GCG CAA CAA GAC TCG CGT CTC GCT      215
Lys Pro His Lys Asp Ser His Tyr Ala Gln Gln Asp Ser Arg Leu Ala
    -30                 -25                 -20

CCG CCT CGG GCT GGC CAC TAC GCT GGG CAT CAG CAC CCA GCC CAG GCC      263
Pro Pro Arg Ala Gly His Tyr Ala Gly His Gln His Pro Ala Gln Ala
    -15                 -10                  -5                  -1

TTC CTG TTC GGC TCC TCG AAC TAC ACC AAG ACC CAG TAC CCG ATC GTC      311
Phe Leu Phe Gly Ser Ser Asn Tyr Thr Lys Thr Gln Tyr Pro Ile Val
  1                   5                  10                  15

CTG ACC CGC GGC ATG CTC GGC TTC GAC AGC CTG CTT GGG GTC GAC TAC      359
Leu Thr Arg Gly Met Leu Gly Phe Asp Ser Leu Leu Gly Val Asp Tyr
                 20                  25                  30

TGG TAC GGC ATT CCC TCA GCC CAG CGT AAA GAC GGC GCC ACC GTC TAC      407
Trp Tyr Gly Ile Pro Ser Ala Gln Arg Lys Asp Gly Ala Thr Val Tyr
             35                  40                  45
```

```
TTC ACC GAA GTC AGC CAG CTC GAC ACC TCC GAA GCC CGG GGT GAG CAA    455
Phe Thr Glu Val Ser Gln Leu Asp Thr Ser Glu Ala Arg Gly Glu Gln
    50              55                  60

CTG CTG ACC CAG GTC GAG GAA ATC GTC GCC ATC AGC GGC AAA CCC AAG    503
Leu Leu Thr Gln Val Glu Glu Ile Val Ala Ile Ser Gly Lys Pro Lys
65              70                  75                      80

GTC AAT CTG TTC GGC CAC AGC CAT GGC GGG CCT ACC ATC CGC TAC GTT    551
Val Asn Leu Phe Gly His Ser His Gly Gly Pro Thr Ile Arg Tyr Val
                85              90                  95

GCC GCC GTG GCC CCG GAT CTG GTC GCC TCG GTC ACC AGC ATT GGC GCG    599
Ala Ala Val Ala Pro Asp Leu Val Ala Ser Val Thr Ser Ile Gly Ala
            100                 105                 110

CCG CAC AAG GGT TCG GCC GCC GCC GAC TTC ATC CGC CAG GTG CCG GAA    647
Pro His Lys Gly Ser Ala Ala Ala Asp Phe Ile Arg Gln Val Pro Glu
        115                 120                 125

GGA TCG GCC AGC GAA GCG ATT CTG GCC GGG ATC GTC AAT GGT CTG GGT    695
Gly Ser Ala Ser Glu Ala Ile Leu Ala Gly Ile Val Asn Gly Leu Gly
    130                 135                 140

GCG CTG ATC AAC TTC CTC TCC GGC AGC AGT TCG GAC ACC CCA CAG AAC    743
Ala Leu Ile Asn Phe Leu Ser Gly Ser Ser Ser Asp Thr Pro Gln Asn
145             150                 155                 160

TCG TTG GGC ACG CTG GAG TCG CTG AAC TCC GAA GGC GCC GCA CGG TTC    791
Ser Leu Gly Thr Leu Glu Ser Leu Asn Ser Glu Gly Ala Ala Arg Phe
                165                 170                 175

AAC GCC CGC TTC CCC CAA GGT GTG CCG ACC AGC GCC TGC GGC GAG GGT    839
Asn Ala Arg Phe Pro Gln Gly Val Pro Thr Ser Ala Cys Gly Glu Gly
            180                 185                 190

GAT TAC GTA GTC AAT GGC GTG CGC TAT TAC TCC TGG AGC GGC ACC AGC    887
Asp Tyr Val Val Asn Gly Val Arg Tyr Tyr Ser Trp Ser Gly Thr Ser
        195                 200                 205

CCG CTG ACC AAC ATA CTC GAC CCT TCC GAC CTG CTC CTC GGC GCC ACC    935
Pro Leu Thr Asn Ile Leu Asp Pro Ser Asp Leu Leu Leu Gly Ala Thr
    210                 215                 220

TCC CTG CCA TTC GGT TTC GAG GCC AAC GAT GGT CTG GTC GGA CGC TGC    983
Ser Leu Pro Phe Gly Phe Glu Ala Asn Asp Gly Leu Val Gly Arg Cys
225             230                 235                 240

AGC TCC CGG CTG GGT ATG GTG ATC CGC GAC AAC TAC CGG ATG AAC CAC    1031
Ser Ser Arg Leu Gly Met Val Ile Arg Asp Asn Tyr Arg Met Asn His
                245                 250                 255

CTG GAT GAG GTG AAT CAG ACC TTC GGG CTG ACC AGC ATA TTC GAG ACC    1079
Leu Asp Glu Val Asn Gln Thr Phe Gly Leu Thr Ser Ile Phe Glu Thr
            260                 265                 270

AGC CCG GTA TCG GTC TAT CGC CAG CAA GCC AAT CGC CTG AAG AAC GCC    1127
Ser Pro Val Ser Val Tyr Arg Gln Gln Ala Asn Arg Leu Lys Asn Ala
        275                 280                 285

GGG CTC TGA                                                         1136
Gly Leu  *
290
```

( 2 ) INFORMATION FOR SEQ ID NO:3:

( i ) SEQUENCE CHARACTERISTICS:
        ( A ) LENGTH: 338 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Leu Pro Asp Ser Leu Cys Asp Ala Val Arg Asp Thr Thr Thr Ile
        -45                 -40                 -35
```

| | | | | | | | | | | | | | |
|---|---|---|---|---|---|---|---|---|---|---|---|---|---|
| Lys | Pro | His<br>-30 | Lys | Asp | Ser | His | Tyr<br>-25 | Ala | Gln | Gln | Asp | Ser<br>-20 | Arg | Leu | Ala |
| Pro | Pro<br>-15 | Arg | Ala | Gly | His | Tyr<br>-10 | Ala | Gly | His | Gln | His<br>-5 | Pro | Ala | Gln | Ala<br>-1 |
| Phe<br>1 | Leu | Phe | Gly | Ser<br>5 | Ser | Asn | Tyr | Thr | Lys<br>10 | Thr | Gln | Tyr | Pro | Ile<br>15 | Val |
| Leu | Thr | Arg | Gly<br>20 | Met | Leu | Gly | Phe | Asp<br>25 | Ser | Leu | Leu | Gly | Val<br>30 | Asp | Tyr |
| Trp | Tyr | Gly<br>35 | Ile | Pro | Ser | Ala | Gln<br>40 | Arg | Lys | Asp | Gly | Ala<br>45 | Thr | Val | Tyr |
| Phe | Thr | Glu<br>50 | Val | Ser | Gln | Leu<br>55 | Asp | Thr | Ser | Glu | Ala<br>60 | Arg | Gly | Glu | Gln |
| Leu<br>65 | Leu | Thr | Gln | Val | Glu<br>70 | Glu | Ile | Val | Ala | Ile<br>75 | Ser | Gly | Lys | Pro | Lys<br>80 |
| Val | Asn | Leu | Phe | Gly<br>85 | His | Ser | His | Gly | Gly<br>90 | Pro | Thr | Ile | Arg | Tyr<br>95 | Val |
| Ala | Ala | Val | Ala<br>100 | Pro | Asp | Leu | Val | Ala<br>105 | Ser | Val | Thr | Ser | Ile<br>110 | Gly | Ala |
| Pro | His | Lys<br>115 | Gly | Ser | Ala | Ala | Ala<br>120 | Asp | Phe | Ile | Arg | Gln<br>125 | Val | Pro | Glu |
| Gly | Ser<br>130 | Ala | Ser | Glu | Ala | Ile<br>135 | Leu | Ala | Gly | Ile | Val<br>140 | Asn | Gly | Leu | Gly |
| Ala<br>145 | Leu | Ile | Asn | Phe | Leu<br>150 | Ser | Gly | Ser | Ser | Asp<br>155 | Thr | Pro | Gln | Asn<br>160 |
| Ser | Leu | Gly | Thr | Leu<br>165 | Glu | Ser | Leu | Asn | Ser<br>170 | Glu | Gly | Ala | Ala | Arg<br>175 | Phe |
| Asn | Ala | Arg | Phe<br>180 | Pro | Gln | Gly | Val | Pro<br>185 | Thr | Ser | Ala | Cys | Gly<br>190 | Glu | Gly |
| Asp | Tyr | Val<br>195 | Val | Asn | Gly | Val | Arg<br>200 | Tyr | Tyr | Ser | Trp | Ser<br>205 | Gly | Thr | Ser |
| Pro | Leu<br>210 | Thr | Asn | Ile | Leu | Asp<br>215 | Pro | Ser | Asp | Leu | Leu<br>220 | Leu | Gly | Ala | Thr |
| Ser<br>225 | Leu | Pro | Phe | Gly | Phe<br>230 | Glu | Ala | Asn | Asp | Gly<br>235 | Leu | Val | Gly | Arg | Cys<br>240 |
| Ser | Ser | Arg | Leu | Gly<br>245 | Met | Val | Ile | Arg | Asp<br>250 | Asn | Tyr | Arg | Met | Asn<br>255 | His |
| Leu | Asp | Glu | Val<br>260 | Asn | Gln | Thr | Phe | Gly<br>265 | Leu | Thr | Ser | Ile | Phe<br>270 | Glu | Thr |
| Ser | Pro | Val<br>275 | Ser | Val | Tyr | Arg | Gln<br>280 | Gln | Ala | Asn | Arg | Leu<br>285 | Lys | Asn | Ala |
| Gly | Leu<br>290 | | | | | | | | | | | | | | |

( 2 ) INFORMATION FOR SEQ ID NO:4:

( i ) SEQUENCE CHARACTERISTICS:
        ( A ) LENGTH: 1088 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 66..1088

( x i ) SEQUENCE DESCRIPTION: SEQ ID NO:4:

```
ATCGCCTGAA GAACGCCGGG CTCTGAAATA GGCTCCACAA CCAGACAGGG CTGGCCTCAG     60
```

-continued

| | | | | | | | | | | | | | | | | |
|---|---|---|---|---|---|---|---|---|---|---|---|---|---|---|---|---|
| GGGCC | ATG | CAC | AGG | TAC | CGA | TAT | CGA | CAT | GAA | GCC | GCT | GAT | TTA | TCT | | 107 |
| | Met 295 | His | Arg | Tyr | Arg 300 | Tyr | Arg | His | Glu | Ala 305 | Ala | Asp | Leu | Ser | | |
| GCC | GTT | GCT | ACT | CGG | CCT | CGG | CTG | CTC | GGC | TGG | CAC | CTG | AGC | ACA | CCG | 155 |
| Ala | Val 310 | Ala | Thr | Arg | Pro 315 | Arg | Leu | Leu | Gly | Trp 320 | His | Leu | Ser | Thr | Pro | |
| ACA | CCC | AGC | CCC | TCC | GCG | CCC | ACA | TCA | ACG | CCG | CTA | CAA | GCC | GGC | AGT | 203 |
| Thr 325 | Pro | Ser | Pro | Ser 330 | Ala | Pro | Thr | Ser | Pro 335 | Leu | Gln | Ala | Gly | Ser 340 | | |
| GAA | CAA | CCC | GCC | ACA | ACT | CCT | GTG | AGT | CTG | ACC | CGT | CCG | ACC | ACG | CGC | 251 |
| Glu | Gln | Pro | Ala | Thr 345 | Thr | Pro | Val | Ser | Leu 350 | Thr | Arg | Pro | Thr | Thr 355 | Arg | |
| AGC | ACC | GAC | CAG | CAC | CTG | CCC | GCC | TCA | CTG | CGC | GAT | ACC | GAC | ATC | GAT | 299 |
| Ser | Thr | Asp | Gln 360 | His | Leu | Pro | Ala | Ser 365 | Leu | Arg | Asp | Thr | Asp 370 | Ile | Asp | |
| GGT | CAA | CTG | GAA | GTC | GAC | GCC | CAG | GGC | AAT | CTG | GTG | ATT | ACC | GAC | CAA | 347 |
| Gly | Gln | Leu | Glu 375 | Val | Asp | Ala | Gln | Gly 380 | Asn | Leu | Val | Ile | Thr 385 | Asp | Gln | |
| CTG | CGT | CAC | CTG | TTC | GAT | TAT | TTC | TTC | AGC | ACC | GTC | GGC | GAA | CAG | TCG | 395 |
| Leu | Arg | His 390 | Leu | Phe | Asp | Tyr | Phe 395 | Phe | Ser | Thr | Val | Gly 400 | Glu | Gln | Ser | |
| TTC | GAG | CAG | GCC | AGC | AGC | GCT | ATC | CGT | GAC | TAT | CTG | GCC | AGC | CAG | CTG | 443 |
| Phe 405 | Glu | Gln | Ala | Ser | Ser 410 | Ala | Ile | Arg | Asp | Tyr 415 | Leu | Ala | Ser | Gln | Leu 420 | |
| CGT | GAC | GCG | GCT | CTG | GCT | CAG | GCC | CTG | GAT | CTT | CTG | GAT | CGC | TAT | ATC | 491 |
| Arg | Asp | Ala | Ala | Leu 425 | Ala | Gln | Ala | Leu | Asp 430 | Leu | Leu | Asp | Arg | Tyr 435 | Ile | |
| GAC | TAC | AAA | ACT | GAG | CTG | GTG | GAG | CTG | GAG | CGA | CGC | TTC | CCG | ATG | GTG | 539 |
| Asp | Tyr | Lys | Thr 440 | Glu | Leu | Val | Glu | Leu 445 | Glu | Arg | Arg | Phe | Pro 450 | Met | Val | |
| ACC | GAA | CTG | GAC | GGC | CTG | CGC | GCC | CGC | GAA | GAT | GCC | GTA | CAA | CGC | CTG | 587 |
| Thr | Glu | Leu | Asp 455 | Gly | Leu | Arg | Ala | Arg 460 | Glu | Asp | Ala | Val | Gln 465 | Arg | Leu | |
| CGC | GCC | AGT | CTG | TTC | AAC | GCG | CAG | GAG | CAC | GCC | GCC | TTC | TTC | GCC | AGC | 635 |
| Arg | Ala | Ser 470 | Leu | Phe | Asn | Ala | Gln 475 | Glu | His | Ala | Ala | Phe 480 | Phe | Ala | Ser | |
| GAA | GAG | GTC | TAT | AAC | CAG | TTC | ACT | CTT | GAG | CGT | CTG | GCG | ATA | CTG | CAC | 683 |
| Glu 485 | Glu | Val | Tyr | Asn | Gln 490 | Phe | Thr | Leu | Glu | Arg 495 | Leu | Ala | Ile | Leu | His 500 | |
| GAT | CCG | TCG | CTG | GAT | CCG | CAG | ACA | CAG | GCC | GAA | CGG | ATT | GAA | CGG | CTG | 731 |
| Asp | Pro | Ser | Leu | Asp 505 | Pro | Gln | Thr | Gln | Ala 510 | Glu | Arg | Ile | Glu | Arg 515 | Leu | |
| CGC | GAA | GGG | CTG | CCC | GAC | GAG | TTG | CAA | CAA | TTG | CTG | GTA | CCG | CAA | TTG | 779 |
| Arg | Glu | Gly | Leu 520 | Pro | Asp | Glu | Leu | Gln 525 | Gln | Leu | Leu | Val | Pro 530 | Gln | Leu | |
| CAC | CTG | ACC | CTG | CGC | CAC | GAC | CCA | GCA | GTT | GCT | GAC | CAA | GGT | GCC | GAG | 827 |
| His | Leu | Thr 535 | Leu | Arg | His | Asp | Pro 540 | Ala | Val | Ala | Asp | Gln 545 | Gly | Ala | Glu | |
| CCG | GAA | CAG | CTA | CGC | CAG | TTG | CGC | CTG | AAC | CTG | TTC | GGG | CCT | CAG | GCA | 875 |
| Pro | Glu | Gln 550 | Leu | Arg | Gln | Leu | Arg 555 | Leu | Asn | Leu | Phe | Gly 560 | Pro | Gln | Ala | |
| ACC | GAG | CGG | CTG | GAA | CGG | CTG | GAC | CGC | CAA | CGC | AGC | GAA | TGG | GAT | CAG | 923 |
| Thr 565 | Glu | Arg | Leu | Glu | Arg 570 | Leu | Asp | Arg | Gln | Arg 575 | Ser | Glu | Trp | Asp | Gln 580 | |
| CGC | CTT | GAG | CGG | TTC | AAT | CGC | GAA | CGT | CAG | GCG | ATC | ATC | AGC | CAG | CCG | 971 |
| Arg | Leu | Glu | Arg | Phe 585 | Asn | Arg | Glu | Arg | Gln 590 | Ala | Ile | Ile | Ser | Gln 595 | Pro | |
| GGC | GCG | TGG | ACA | GCG | ACA | AGC | AGG | CCG | CGA | TTG | AGG | CCT | GCT | GCA | CGA | 1019 |
| Gly | Ala | Trp | Thr 600 | Ala | Thr | Ser | Arg | Pro 605 | Arg | Leu | Arg | Pro | Ala 610 | Ala | Arg | |

| GCA | GTT | CAG | CGA | GCA | CGA | GCG | CTC | AGG | GTC | AAT | AGC | CTG | TTG | GAA | CTC | 1067 |
| Ala | Val | Gln | Arg | Ala | Arg | Ala | Leu | Arg | Val | Asn | Ser | Leu | Leu | Glu | Leu | |
| | | 615 | | | | 620 | | | | | | 625 | | | | |

| GAT | AGC | CGC | GCC | GAA | CGC | TAG | 1088 |
| Asp | Ser | Arg | Ala | Glu | Arg | * | |
| | 630 | | | | 635 | | |

(2) INFORMATION FOR SEQ ID NO:5:

(i) SEQUENCE CHARACTERISTICS:
  (A) LENGTH: 340 amino acids
  (B) TYPE: amino acid
  (D) TOPOLOGY: linear (i i) MOLECULE TYPE: protein (x i) SEQUENCE DESCRIPTION: SEQ ID NO:5:

```
Met His Arg Tyr Arg Tyr Arg His Glu Ala Ala Asp Leu Ser Ala Val
 1               5                  10                  15

Ala Thr Arg Pro Arg Leu Leu Gly Trp His Leu Ser Thr Pro Thr Pro
             20                  25                  30

Ser Pro Ser Ala Pro Thr Ser Thr Pro Leu Gln Ala Gly Ser Glu Gln
         35                  40                  45

Pro Ala Thr Thr Pro Val Ser Leu Thr Arg Pro Thr Thr Arg Ser Thr
     50                  55                  60

Asp Gln His Leu Pro Ala Ser Leu Arg Asp Thr Asp Ile Asp Gly Gln
 65                  70                  75                  80

Leu Glu Val Asp Ala Gln Gly Asn Leu Val Ile Thr Asp Gln Leu Arg
                 85                  90                  95

His Leu Phe Asp Tyr Phe Phe Ser Thr Val Gly Glu Gln Ser Phe Glu
            100                 105                 110

Gln Ala Ser Ser Ala Ile Arg Asp Tyr Leu Ala Ser Gln Leu Arg Asp
        115                 120                 125

Ala Ala Leu Ala Gln Ala Leu Asp Leu Leu Asp Arg Tyr Ile Asp Tyr
    130                 135                 140

Lys Thr Glu Leu Val Glu Leu Glu Arg Arg Phe Pro Met Val Thr Glu
145                 150                 155                 160

Leu Asp Gly Leu Arg Ala Arg Glu Asp Ala Val Gln Arg Leu Arg Ala
                165                 170                 175

Ser Leu Phe Asn Ala Gln Glu His Ala Ala Phe Ala Ser Glu Glu
            180                 185                 190

Val Tyr Asn Gln Phe Thr Leu Glu Arg Leu Ala Ile Leu His Asp Pro
        195                 200                 205

Ser Leu Asp Pro Gln Thr Gln Ala Glu Arg Ile Glu Arg Leu Arg Glu
    210                 215                 220

Gly Leu Pro Asp Glu Leu Gln Gln Leu Leu Val Pro Gln Leu His Leu
225                 230                 235                 240

Thr Leu Arg His Asp Pro Ala Val Ala Asp Gln Gly Ala Glu Pro Glu
                245                 250                 255

Gln Leu Arg Gln Leu Arg Leu Asn Leu Phe Gly Pro Gln Ala Thr Glu
            260                 265                 270

Arg Leu Glu Arg Leu Asp Arg Gln Arg Ser Glu Trp Asp Gln Arg Leu
        275                 280                 285

Glu Arg Phe Asn Arg Glu Arg Gln Ala Ile Ile Ser Gln Pro Gly Ala
    290                 295                 300

Trp Thr Ala Thr Ser Arg Pro Arg Leu Arg Pro Ala Ala Arg Ala Val
305                 310                 315                 320
```

Gln Arg Ala Arg Ala Leu Arg Val Asn Ser Leu Leu Glu Leu Asp Ser
                325                     330                335

Arg Ala Glu Arg
            340

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:6:

Phe Leu Phe Gly Ser Ser
1               5

( 2 ) INFORMATION FOR SEQ ID NO:7:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

Phe Leu Phe Gly Ser Ser Asn Tyr Thr Lys Thr Gln Tyr Pro Ile Val
1               5                   10                  15

Leu Thr Arg Gly
            20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

TAATTGGTCA CTTTTCAGCC                         20

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:9:

Gly His Ser His Gly
1               5